United States Patent [19]

Snider

[11] Patent Number: 5,139,326

[45] Date of Patent: Aug. 18, 1992

[54] DISPOSABLE OCCLUDER FOR EYE EXAMINATION

[76] Inventor: Lloyd Snider, 6839 Edinborough, West Bloomfield, Mich. 48322

[21] Appl. No.: 583,191

[22] Filed: Sep. 17, 1990

[51] Int. Cl.$^5$ .............................. G02C 1/00; A61B 3/00
[52] U.S. Cl. ..................................... 351/205; 359/610
[58] Field of Search ............... 351/200, 205, 214, 158; 350/578; 128/745; 359/610

[56] References Cited

U.S. PATENT DOCUMENTS 683,012  9/1901  Hill ....................................... 350/578

Primary Examiner—Rodney B. Bovernick
Attorney, Agent, or Firm—Reising, Ethington, Barnard, Perry & Milton

[57] ABSTRACT

An optical occluder (10) includes a support or handle portion (12) and an occluding portion (14) connected to the handle (12) for occluding at least one eye of an individual. The occluding portion (14) includes a surface having a concave shape for allowing freedom of movement of an eyelid of the individual while the occluding portion (14) is placed over the individual's eye. The invention further provides a method of making the optical occluder (10) including the steps of forming the support and occluding portions (12, 14) of the occluder (10) and shaping a surface of the occluding portion (14) into a concave shape.

4 Claims, 1 Drawing Sheet

DISPOSABLE OCCLUDER FOR EYE EXAMINATION

TECHNICAL FIELD

The present invention relates generally to devices having utility in the diagnosis and treatment of eye conditions. More particularly, the present invention relates to devices useful as ophthalmic occluders which block the vision of a patient's one eye while the other eye is being examined. Such occluders are also useful for blocking the vision of one eye while the other eye is viewing through an instrument.

BACKGROUND OF THE INVENTION

Occluders are frequently used by eye care professionals to cover a patient's eye when giving an eye examination. Currentday occluders are not disposable and must be frequently cleaned. If occluders are not sterilized after each use, a patient is at risk of infection.

The U.S. Pat. Nos. 4,824,235 to Eddy, issued Apr. 25, 1989 and U.S. Pat. No. 4,903,706 to Vila-Cora et al, issued Feb. 27, 1990 are examples of optical occluders. The occluders include a support or handle portion and an occluding portion. The occluding portion includes two flat surfaces.

The present invention provides an occluder which allows for freedom of movement of an eyelid of an individual while the occluder is placed over the individual's eye. Such an occluder is well suited to be made from inexpensive materials, such as heavy paper. Accordingly, the present invention can easily be made at a low cost and thereby be disposable and not require the sterilizing step after use or the sterilizing equipment necessary for such operations.

SUMMARY OF THE INVENTION

In accordance with the present invention, there is provided an optical occluder including a support and occluding means connected to the support for occluding at least one eye of an individual. The occluding means occludes a surface having a concave shape for allowing freedom of movement of an eyelid of the individual while the occluding means is placed over the individual's eye.

The present invention further provides a method of making the optical occluder. The method includes the steps of forming support and occluding portions of the occluder and shaping a surface of the occluding portion into a concave shape.

FIGURES IN THE DRAWINGS

Other advantages of the present invention will be readily appreciated as the same becomes better understood by reference to the following detailed description when considered in connection with the accompanying drawings wherein:

FIG. 1 is a plan view of an optical occluder made in accordance with the present invention; and FIG. 2 is an edge on view of the occluder taken substantially along lines 2—2 of FIG. 1.

DETAILED DESCRIPTION OF THE INVENTION

Figure 1:
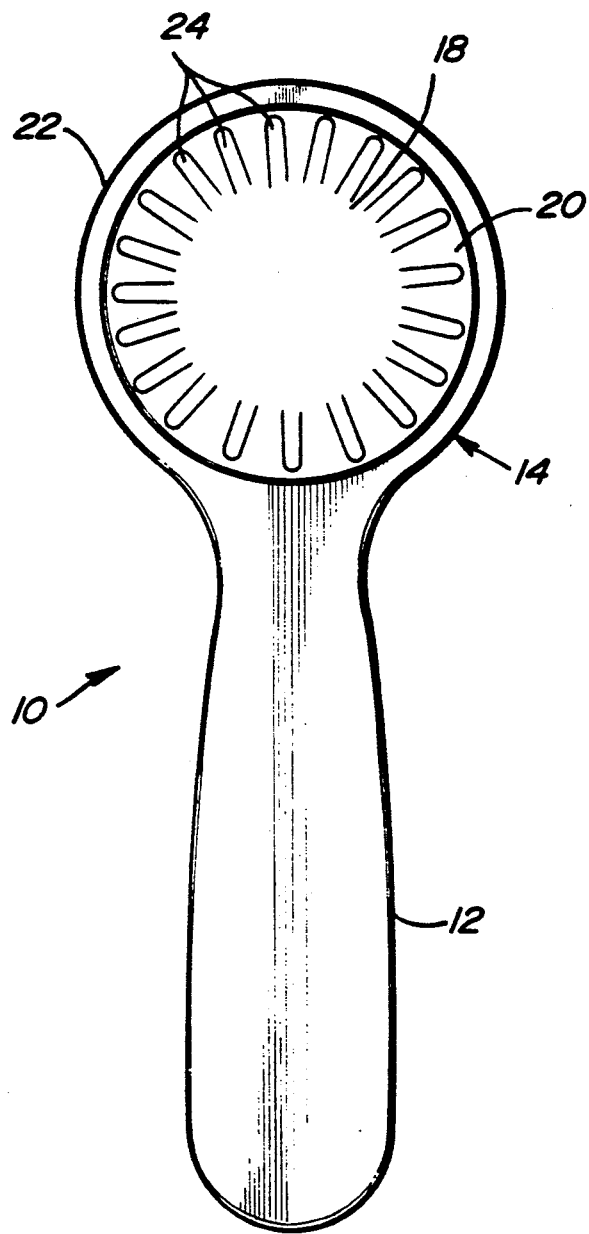
Figure 2:
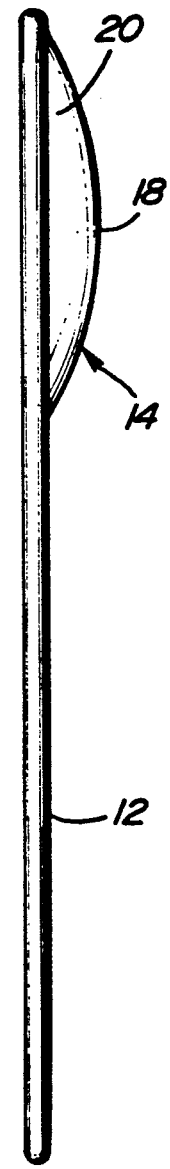

An optical occluder constructed in accordance with the present invention is generally shown at 10 in the drawings. The occluder 10 includes a support or handle portion 12 and an integral plate or occluding portion generally indicated at 14. The occluding portion 14 is integrally connected to the handle portion 12 although the pieces could be made separately and later connected by means of glue or other adhesives.

In the preferred embodiment, the handle 12 and occluding portion 14 are made from a single piece of heavy paper thereby rendering the device inexpensive and suitable for being disposable. By being disposable, the sterilization steps required for the sanitation of prior art occluders is not necessary.

The occluding portion 14 occludes at least one eye of an individual during, for example, the examination of the other eye. Such an occluder could also be used in other situations where one eye is being used for vision and it is preferable to keep the occluded eye open. For example, such an occluder could be used by a person using a telescope, microscope, etc.

The invention is characterized by the occluding means including a surface having a concave shape for allowing freedom of movement of an eyelid of the individual while the occluder means is placed over the individual's eye. In other words, rather than having a flat shaped prior art occluder wherein the eye is either kept open or closed and the occluder blocks any movement of the eyelid, the present invention allows for freedom of movement of the eyelid and increased conformt by the user.

More specifically, the surface of the occluding portion 14 includes a base portion 18 and has a substantially frustoconical portion 20 adjacent thereto extending to a peripheral edge 22 of the occluding portion 14. The combination of the base portion 18 and frustoconical portion 20 defines the concave shape of the surface.

The occluding portion 14 includes stiffening means for stiffening the occluding portion 14 and retaining the concave shape of the surface. This is particularly necessary where the occluder is made from an inexpensive, substantially flexible material such as heavy paper or thin plastic.

The stiffening means can take the form of a plurality of scallops 24 in the surface extending radially outwardly from the base portion 18 to the peripheral edge 22. Of course, the stiffening means could take on other forms which provide rigidity to the surface. The scallops are particularly useful allowing further space form the patient's eyelashes during movement of the eyelid. Thus, the present invention provides a disposable occluder allowing freedom of movement of the patient's eyelids and further is shaped to provide additional comfort to the user by allowing spaces for the patient's eyelashes to have access to when the eyelids are open.

The present invention further provides a method of making the optical occluder, including the steps of forming the support and occluding portions 12,14 of the occluder 10 and then shaping a surface of the occluding portion 14 into the concave shape.

More specifically, the support and occluding portions 12,14 can be cut from a sheet of material thereby in a single cutting step forming the handle portion 12 and occluder portion 14. The scallops 24 can then be pressed into the occluder portion 14 thereby forming the concave shape of the occluder portion 14 while stiffening the portion in the single step. Thusly, the present invention provides a two step process for forming the disposable occluder in accordance with the present invention.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. An optical occluder (10) comprising: a support (12); occluding means (14) connected to said support (12) for occluding at least one eye of an individual, said occluding means (14) including a surface having a concave shape for allowing freedom of movement of an eyelid of the individual while said occluding means (14) is placed over the individual's eye, said support including an elongated handle portion (12), said occluding means (14) being integrally connected to said handle portion (12); and stiffening means for stiffening said occluding means (14) and retaining said concave shape of said surface, said surface including a base portion (18) and a substantially frustoconical portion (20) adjacent thereto extending to a peripheral edge (22) of said occluding means (14) defining said concave shape of said surface, said stiffening means including a plurality of scallops (24) in said surface extending radially outwardly from said base portion (18) to about said peripheral edge (22).

2. A method of making an optical occluder (10), said method including the steps of forming support and occluder portions (12,14) of the occluder (10) and shaping a surface of the occluding portion (14) into a concave shape stiffening the concave occluder portion while retaining the concave shape of the surface and forming radially outwardly extending stiffening scallops (24) in the occluder portion (14).

3. A method as set forth in claim 4 wherein said forming step is further defined as cutting the support and an occluding portion (12,14) integral therewith from a sheet of material.

4. A method as set forth in claim 2 wherein said shaping step is further defined as pressing the occluder portion (14) into the concave shape.

* * * * *